United States Patent [19]

Hait et al.

[11] Patent Number: 5,104,858

[45] Date of Patent: Apr. 14, 1992

[54] SENSITIZING MULTIDRUG RESISTANT CELLS TO ANTITUMOR AGENTS

[75] Inventors: William N. Hait; James M. Ford, both of New Haven, Conn.

[73] Assignee: Yale University, New Haven, Conn.

[21] Appl. No.: 250,891

[22] Filed: Sep. 29, 1988

[51] Int. Cl. .......................... A61K 31/70; A61K 31/38
[52] U.S. Cl. ........................................ 514/34; 514/437
[58] Field of Search .................. 435/240.3, 240.31; 514/224.5, 34, 437; 549/27

[56] References Cited

FOREIGN PATENT DOCUMENTS 863699 3/1961 United Kingdom .
925538 5/1963 United Kingdom .

OTHER PUBLICATIONS

Ganapathi, et al. Enhancement of Sensitivity to Adriamycin in Resistant P388 Leukemia by the . . . Cancer Research, vol. 43, pp. 3696–3699, 1983.
Akiyama, et al. Circumvention of Multiple-Drug Resistance in Human Cancer Cells by Thioridazine, Trifluoperazine . . . 0 JNCI vol. 76, No. 5, pp. 839–844, 1986.
Hait, et al. Calmodulin: A Potential Target for Cancer Chemotherapeutic Agents, J. Clinical Oncology, vol. 4, No. 6, pp. 994–1012, 1986.
Nielson, et al. The Comparative Pharmacology of Flupenthixol and some Reference Neuroleptics, Acta Pharmacol. Toxicol., vol. 33, pp. 353–362, 1973.
Norman, et al. Inhibition of Calcium-Dependent Regulator-. . . Molec. Pharmacol., vol. 16, pp. 1089–1094.
Roufogalis, B. D., "Specificity of Trifluoperazine and Related Phenothiazines for Calcium Binding Proteins", In: W. Y. Cheung (ed.) *Calcium and Cell Function*, vol. III, pp. 129–159, New York, Academic Press, 1982.
Pang, D. C., and Briggs, F. N., "Mechanism of Quinidine and Chlorpromazine Inhibition of Sarcotubular ATPase Activity, *Biochem. Pharmacol.*, 25, 21–25 (1976).

(List continued on next page.)

*Primary Examiner*—John Doll
*Assistant Examiner*—George C. Elliott
*Attorney, Agent, or Firm*—Frishauf, Holtz, Goodman & Woodward

[57] ABSTRACT

A method for sensitizing multidrug resistant cells to antitumor agents comprosing contacting multidrug resistant cells, with an effective amount of a compound of the formula

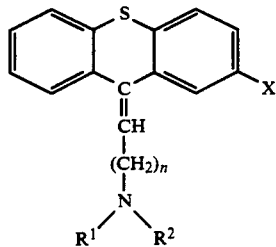

wherein n is 1, 2 or 3, X is $CF_3$, —O—$CH_3$, Br, I, Cl, H, W and S—$CH_3$ and $R^1$ and $R^2$, independently of each other are —$CH_3$—$CH_2$—$CH_3$, $CH_2CH_2OHCH_2OH$, or $NR^1R^2$ form a ring

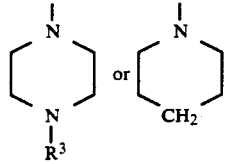

wherein $R^3$ is —$CH_3$, $CH_2$—$CH_3$, —H, $CH_2OH$ and $CH_2CH_2OH$.

6 Claims, 5 Drawing Sheets

OTHER PUBLICATIONS

Ruben, L. and Rasmussen, H., "Phenothiazines and Related Compounds Disrupt Mitochondrial Energy Production by a Calmodulin-Independent Reaction", *Biochem. Biophys. Acta.*, 637, 415-422 (1981).

Creese, I., and Sibley, D. R., "Receptor Adaptations to Centrally Acting Drugs", *Ann. Rev. Pharmacol. Toxicol.*, 21, 357-391 (1980).

Levin, R. M. and Weiss, B., "Mechanism by which Psychotropic Drugs Inhibit Adensine Cyclic 3', 5'-Monophosphate PDE of Brain" *Mol. Pharmacol.*, 12, 581-589 (1976).

Manalan, A. S. and C. B. Klee, "Calmodulin, *Adv. Cyclic Nucleotide Protein Phosphorylation Res.*, 18, 227-278 (1984).

Veigl, M. L., Vanaman, T. C., and Sedwick, W. D., "Calcium and Calmodulin in Cell Growth and Transformation", *Biochem, Biophys. Acta.* 738, 21-48 (1984).

Rasmussen, C. D. and Means, A. R., "Calmodulin-Regulation of Cell Proliferation" *EMBO*, 6, 3961-3968 (1987).

Wei, J. W., Hickie, R. A., and Klaassen, D. J., "Inhibition of Human Breast Cancer Colony Formation by Anticalmodulin Agents: Trifluoperazine, W-7, and W-13", *Cancer Chemother. Pharmacol.*, 11, 86-90 (1983).

Ito, H., and Hidaka, H., "Antitumor Effect of a Calmodulin Antagonist on the Growth of Solid Sarcoma", *Cancer Lett:* 19, 215-220 (1983).

Hait, W. N., Grais, L., Benz, C., Cadman, E., "Inhibition of Growth of Leukemic Cells by Inhibitors of Calmodulin: Phenothiazines and Melittin", *Cancer Chemother. Pharmacol.* 14, 202-205 (1985).

Riordan, J. R. and Ling, V., "Genetic and Biochemical Characterization of Multidrug Resistance", *Pharmol. Ther.*, 28, 51-75 (1985).

Inaba, M., Johnson, R. K., "Uptake and Retention of Adriamycin and Daunonubicin by Sensitive and Anthracycline-Resistant Sublines of P388 Leukemia", *Biochem. Pharmacol.*, 27, 2123-2130 (1978).

Fojo, A. S., Akiyama, M. M. Gottesman, and I. Pastan, "Reduced Drug Accumulation in Multiple-Drug Resistant Human KB Carcinoma Cell Lines", *Cancer Res.*, 45, 3002-3007 (1985).

Chen, C., Chin. J. E., K. Ueda, Clark, C. P., Pastan, I., Gottesman, M. M., and Roninson, I. B., "Internal Duplication and Homology with Bacterial Transport Proteins in the *mdrl* (P-glycoprotein) Gene from Multidrug Resistant Human Cells", *Cell*, 47, 381-389 (1986).

Hamada, H., and Tsuruo, T., "Purification of the 170-to-180Kilodalton Membrane Glycoprotein Associated with MDR; 170-180Kilodalton Membrane Glyceprotein is an ATPase, *J. Biol. Chem.*, 263, 1454-1458 (1988).

Akiyama, S., Cornwell, M. M., Kuwano, M., Pastan, I., and Gottesman, M. M., "Most Drugs that Reverse Multidrug Resistance Also Inhibit Photoaffinity Labeling of P-glycoprotein by a Vinblastine Analog", *Mol. Pharmacol.*, 33, 144-147 (1988).

Fleckenstein, A., "Specific Pharmacology of Calcium in Myocardium, Cardiac Pacemakers, and Vascular Smooth Muscle:, *Ann. Rev. Pharmacol. Toxicol.*, 17, 149-166 (1977). Mori, T., Takai, Y., Minakuchi, Yu, B., Nishizuka, Y., "Inhibitory Action of Chlorpromazine, Dibucaine, and other Phospholipid-Interacting Drugs on Calcium-Activated, Phospholipid-Dependent Protein Kinase", *J. Biol. Chem.*, 255, #18, 8378-8380 (1980).

Prozialeck, W. C. and Weiss, B., "Inhibition of Calmodulin by Phenothiazines and Related Drugs: Structure-Activity Relationships", *J. Pharmacol. Exp. Ther.*, 222, 509-516 (1982).

Hidaka, H., Asano, M., T. Tanaka, "Activity-Structure Relationship of Calmodulin Antagonists", *Mol. Pharmacol.*, 20, 571-578 (1981).

MacNeil, S., Griffin, M., Cooke, A. M., Pettett, N. J., Dawson, R. A., Blackburn, G. M., "Calmodulin Antagonists of Improved Potency and Specificity for use in the Study of Calmodulin Biochemistry", *Biochem. Pharmacol.*, 37, 1717-1723 (1988).

Reid, R. E., "Drug Interactions with Calmodulin: The Binding Site", *J. Theor. Biol.*, 105, 63-76 (1983).

Miller, Robin L., et al., *Journal of Clinical Oncology*, vol. 6, No. 5, May 1988, 880-888.

Roufogalis, B. D., "Comparative Studies on the Membrane Actions of Depressant Drugs: The Role of Lipophilicity in the Inhibition of Brain Sodium and Potassium-Stimulated ATPase", *J. Neurochem.*, 24, 51-61 (1975).

G. L. Lee and W. N. Hait, "Inhibition of Growth of $C_6$ Astrocytoma Cells by Inhibitors of Calmodulin", *Life Sci.*, 36, 347-354, (1985).

OTHER PUBLICATIONS

W. N. Hait and G. L. Lee, "Characteristics of the Cytotoxic Effect of the Phenothiazine Class of Calmodulin Antagonists, *Biochem. Pharmacology*, 34, 3973–3978, (1985).

Ganapathi, R., Grabowski, D., Turinic, R., and Valenzuela, R., "Correlation Between Potency of Calmodulin Inhibitors and Effects on Cellular Levels of Cytotoxic Activity of Doxorubicin (Adriamycine) in Resistant P388 Mouse Leukemia Cells", *Eur. J. Cancer Clin. Oncol.*, 20, 799–806 (1984).

Gros, P., Ben Neriah, Y., Croop, J. M., Housman, D. E., "Isolation and Expression of a cDNA (mdr) that Confers Multidrug Resistance", *Nature*, 323, 728–731 (1986).

Ueda, K., Cardarelli, C., Gottesman, M. M., Pastan, I., "Expression of a Full-Length cDNA for the Human mdr1 Gene Confers Resistance to Colchicino, Doxorubicin and Vinblastine", *Proc. Natl. Acad. Sci. U.S.A.*, 84, 3004–3008 (1987).

Cornell, M. M., Pastan, I., Gottesman, M. M. "Certain Calcium Channel Blockers Blind Specifically to Multidrug Resistant Human KB Carcinoma Membrane Vesicles & Inhibit Drug Binding to P-glycoprotein", *J. Biol. Chem.*, 262, 2166–2170 (1987).

Raess B. U., Vincenzi F. F., "Calmodulin Activation of Red Blood Cells ($Ca^{2+}+Mg^{2+}$)-ATPase and Its Antagonism by Phenothiazines", *Mol. Pharmacol.*, 18, 253–258 (1980).

Center, M. C., "Mechanisms Regulating Cell Resistance to Adriamycin", *Biochem. Pharmacol*, 34, 1471–1476 (1985).

Ido, M., Asao, T., Sakurai, M., Inagaki, M., Saito, M., Hidaka, H., "An Inhibitor of Protein Kinase C, 1-(-5-isoquinolinylsulfonyl)-2-methylpiperazine (H-7) Inhibits TPA–Induced Reduction of Vincristine Uptake from P388 Murine Leukemic Cell," *Leukemia Res.* 10, 1063–1069 (1986).

Ferguson, P. F., Cheng, Y., "Transient Protection of Cultured Human Cells Against Antitumor Agents by 12-O-tetradecanolyphorbol-13-acetate", *Cancer Res.*, 47, 433–441 (1987).

Fine R. L., Patel, J., Chabner, B. A., "Phorbol Esters Induce Multidrug Resistance in Human Breast Cancer Cells", *Proc. Natl. Acad. Sci. U.S.A.*, 85, 582–586 (1988).

Palayoor, S. T., Stein, J. M. Hait W. N., "Inhibition of (List continued on next page.)

Protein Kinase C by Antineoplastic Agents: Implications for Drug Resistance", *Biochem. Biophys. Res. Commun*, 148, 718–725 (1987).

Ganapathi, R., Grabowski, D., "Differential Effect of the Calmodulin Inhibitor Trifluoperazine on Cellular Accumulation, Retention and Cytoxicity of Anthracyclines in Doxorubicin in Doxorubicin-(Adriamycin) Resistant P388 Mouse Leukemia Cells", *Cancer Research*, 44, 5056–5061 (1984).

Ahn, C. H., Fine R. L., Anderson, W. B., "Possible Involvement of Protein Kinase C in the Modulation of Multidrug Resistance", *Proc. Am. Assoc. Cancer Res.* 29 1182 (1988).

Schatzman, R. C., Wise, B. C., Kuo J. F., "Phospholipid–Sensitive Calcium Dependent Protein Kinase: Inhibition by Anti–Psychotic Drugs", *Biochem. Biophys. Res. Commun.*, 98, 669–676 (1981).

Huff, R. M. Molinoff, B., "Assay of Dopamine Receptors with [alpha-$^3$H] Flupenthioxol, *J. Pharmacol. Exp. Ther.*, 232, 57–61 (1984).

Post, M. L., Kennard, U., Horn, A. S., "Stereoselective Blockade of the Dopamine Receptor and the X-ray Structures of Alpha and Beta-flupenthoxil", *Nature*, 256, 342–343 (1975).

Hait, W. N., Lazo, J. S. Chen, D. L., Gallicchio, V., "Preclinical and Phase I–II Studies of Bleomycin (BLEO) with Calmodulin-Antagonist (CaM-A)", *Proc. Am. Assoc. Cancer Res.*, 26, 1283 (1985).

Johnstone, et al., *The Lancet*, "Mechanism of the Anti-Psychotic Effect in the treatment of Acute Schizophrenia", Apr. 22, 1978.

Finlay, G. J., B. C. Baguley, "The Use of Human Cancer Cell Lines as a Primary Screening System for Antineoplastic Compounds", *Eur. J. Cancer Clin. Oncol.*, 20, 947–954 (1984).

Berenbaum, M. C., "Criteria for Analyzing Interactions Between Biologically Active Agents", *Adv. Ca. Res.*, 35, 369–335, (1981).

pastan, I., and Gottesman, M., "Multiple Drug Resistance in Human Cancer", *New England Journal of Medicine*, pp. 1388–1393, May 28, 1987.

Ganapathi, R., and Grabowski, D., "Differential Effect of the Calmodulin Inhibitor Trifluoperazine in Modulating Cellular Accumulation, Retention and Cytoxicity of Doxorubicin in Progressively Doxorubicin–Resistant L1210 Mouse Leukemia Cells", *Biochem. Pharmacol.*, 37, 185–194, (1988).

OTHER PUBLICATIONS

Finlay, G. J., Baguley, B. C., and Wilson, W. R., "A Semiautomated Microculture Method for Investigating Exponentially Growing Carcinoma Cells", *Anal. Biochem.*, 139, 272-277 (1984).

Ganapathi, R., Grabowski, D., and Schmidt, H., "Factors Governing the Modulation of Vinca-alkaloid Resistance in Doxorubicin-resistant Cells by the Calmodulin Inhibitor Trifluoperazine", *Biochem. Pharmacol.*, 35: 673-678 (1986).

Uzunov, P., and Weiss, B., "Psychopharmacological Agents and the Cyclic AMP System of Rat Brain", *Adv. Cyclic Nucleotide Res.*, 1:435-453 (1972).

Levin, R. M., and Weiss, B., "Binding of Trifluoperazine to the Calcium-dependent Activator of Cyclic Nucleotide PDE", *Mol. Pharmacol.*, 13: 690-697, (1977).

Levin, R. M., and Weiss, B., "Selective Binding of Antipsychotics and Other Psychoactive Agents to the Calcium-dependent Activator of Cyclic Nucleotide PDE", *J. Pharmacol. Exp. Ther.*, 208:454-459 (1979).

Weiss, B., "Techniques for Measuring the Interaction of Drugs with Calmodulin", In: A. R. Means and B. W. O'Malley (eds) *Hormone Action: Calmodulin and Calcium-Binding Proteins.*, vol. 102, pp. 171-184, New York: Academic Press (1983).

Cheung, W. Y., "Calmodulin Plays a Pivitol Role in Cellular Regulation", *Science*, 207: 19-27 (1980).

Vanaman, T. V., "Structure, Function and Evolution of Calmodulin", In: W. Y. Cheung (ed.), *Calcium and Cell Function*, vol. 1, pp. 41-48, New York: Academic Press (1980).

Osborn, M., and Weber, K., "Damage of Cellular Functions by Trifluoperazine, a Calmodulin-Specific Drug", *Exp. Cell. Res.*, 130-484-488 (1980).

Beck, W., "The Cell Biology of Multiple Drug-Resistance", *Biochem. Pharmacol.*, 36: 2879-2887, (1987).

Wise, B. C., Glass, D. B., Chou, C., -H. J., Raynor, R. L., Katoh, N., Schatzman, R. C., Turner, R. S., Kibler, R. F., Kuo, J. F., "Phospholipid-Sensitive $Ca^{2+}$ Dependent Protein Kinase from Heart.II. Substrate Specificity and Inhibition by Various Agents", *J. Biol. Chem.*, 257:8489-8495 (1982).

Proceeding of the American Association for Cancer Research, vol. 30, Mar. 1989, p. 570.

Molecular Pharmacology, vol. 35, No. 1, 1989, pp. 105-115.

Cancer Treatment Reports, vol. 62, No. 1, Jan. 1978, pp. 45-74.

Gann, vol. 61, No. 6, Dec. 1970, pp. 529-534.

Journal of Clinical Oncology, vol. 6, No. 5, May 1988, pp. 880-888.

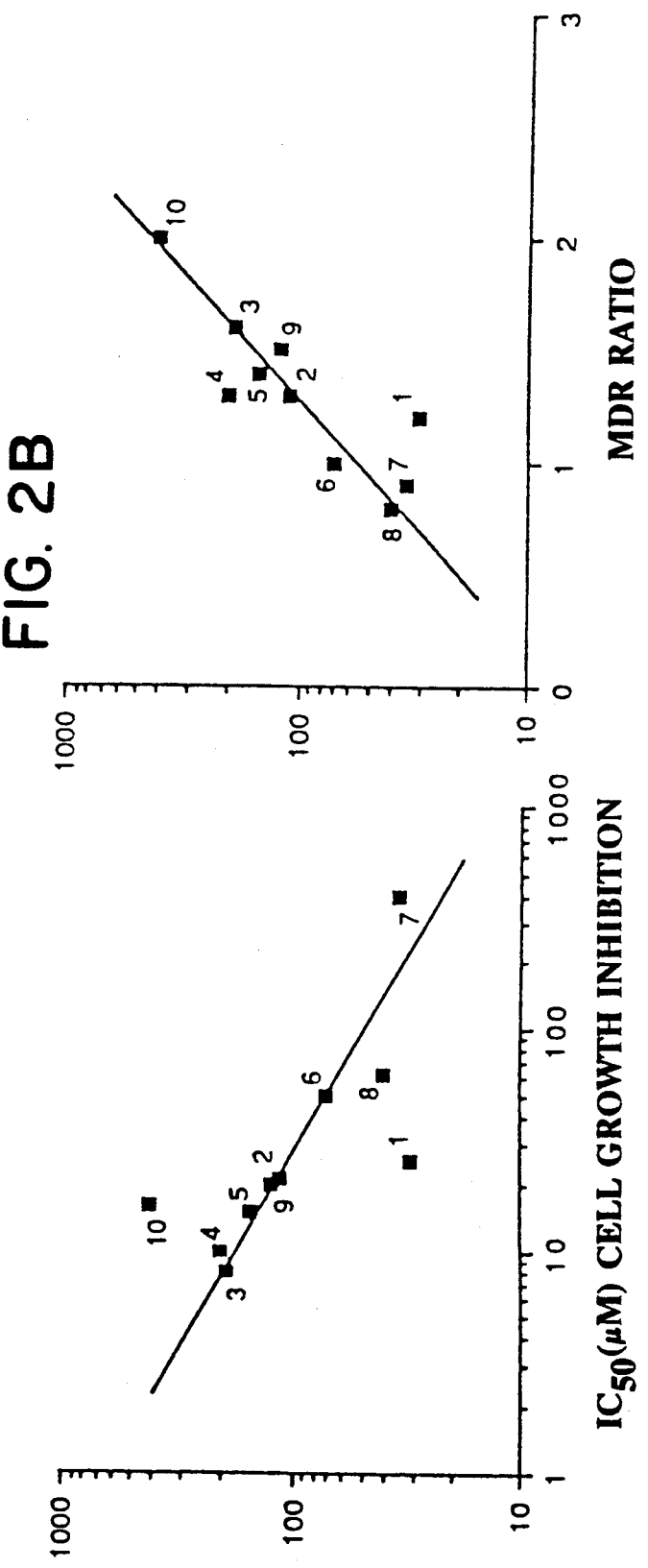

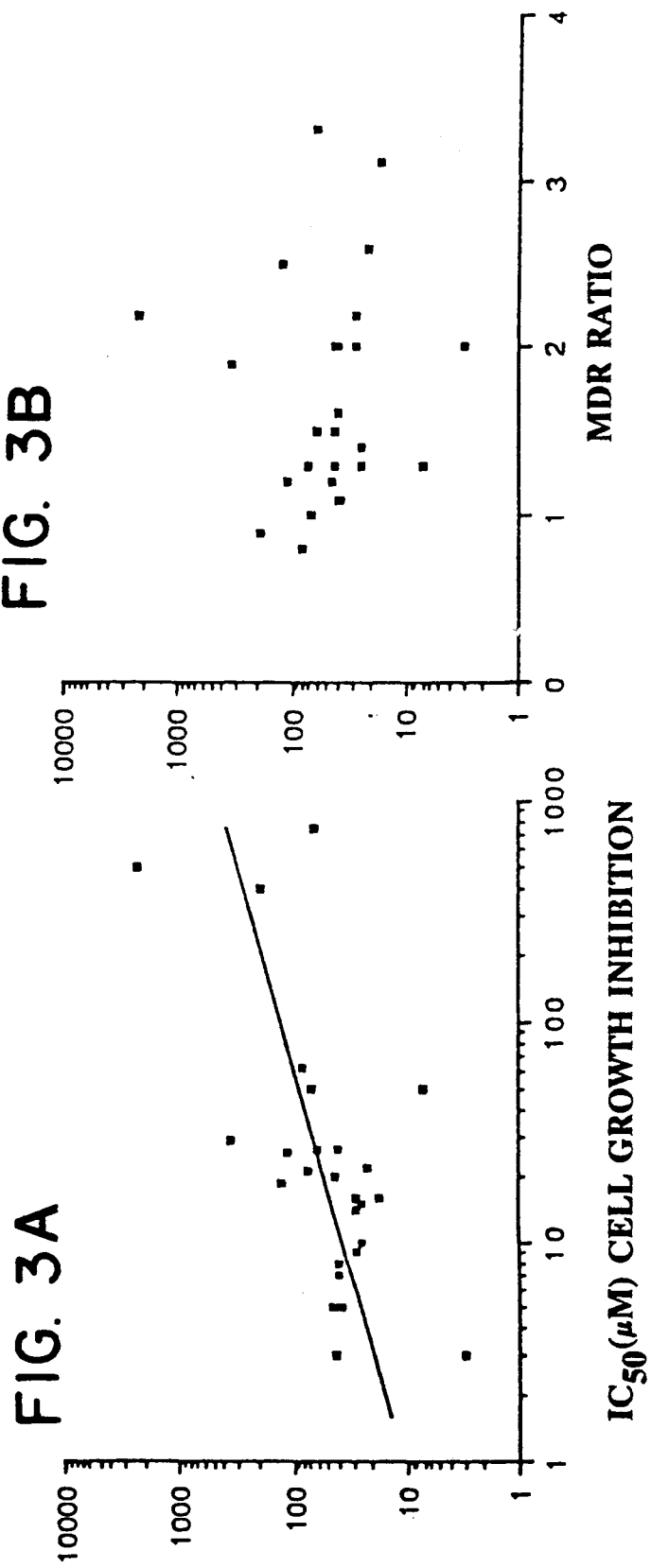

SENSITIZING MULTIDRUG RESISTANT CELLS TO ANTITUMOR AGENTS

BACKGROUND OF THE INVENTION

1. Field of the Invention

The present invention concerns a method of sensitizing multidrug resistant (MDR) cells to antitumor agents using phenothiazines (PTZs) and thioxanthenes.

2. Background of the Invention

Phenothiazines and structurally related antipsychotic agents inhibit several cellular enzymes and block the function of critical cellular receptors (Roufogalis, B. D. "Specificity of Trifluoperazine and Related Phenothiazines for Calcium Binding Proteins", In: W. Y. Cheung (ed.) *Calcium and Cell Function*, Vol III, pp. 129-159, New York, Academic Press, 1982; Pang D. C. and Briggs, F. N., "Mechanism of Quinidine and Chlorpromazine Inhibition of Sarcotubular ATPase Activity, *Biochem. Pharmacol.*, 25, 21-25, (1976); Ruben, L. and Rasmussen, H., "Phenothiazines and Related Compounds Disrupt Mitochondrial Energy Production by a Calmodulin-Independent Reaction", *Biochim. Biophys. Acta.*, 637, 415-422 (1981); Creese, I., and Sibley, D. R., "Receptor Adaptations to Centrally Acting Drugs", *Ann.Rev. Pharmacol. Toxicol.*, 21, 357-391, (1980)).

Prominant among the cellular targets is calmodulin (CaM), the multifunctional calcium binding protein (Levin, R. M., and Weiss, B., "Mechanism By Which Psychotropic Drugs Inhibit Adensine Cyclic 3',5'-monophosphate PDE of Brain", *Mol. Pharmacol.*, 12, 581-589 (1976)).

CaM has been implicated in the regulation of numerous cellular events (Manalan, A. S. and C. B. Klee, "Calmodulin", *Advances In Cyclic Nucleotide Protein Phosphorylation Res.*, 18,227-278 (1984) including that of normal (Veigl, M. L. Vanaman, T. C., and Sedwick, W. D., "Calcium and Calmodulin in Cell Growth and Transformation", *Biochem. Biophys. Acta.*, 738, 21-48, (1984)) and abnormal cellular proliferation (Hait, W. N. and Lazo, J. S. "Calmodulin, "A Potential Target for Cancer Chemotherapeutic Agents", *J. Clin. Oncol.*, 4, 994-1012 (1986)); Rasmussen, C. D. and Means, A. R., "Calmodulin - Regulation of Cell Proliferation", *EMBO*, 6, 3961-3968 (1987); Wei, J. W., R. A. Hickie, and D. J. Klaassen, "Inhibition of Human Breast Cancer Colony Formation by Anticalmodulin Agents: Trifluoperazine, W-7, and W-13", *Cancer Chemother. Pharmacol.*, 11, 86-90 (1983)). Consistent with these observations was the demonstration that PTZs and other CaM antagonists possess antiproliferative and cytotoxic effects (Ito, H., and H. Hidaka, "Antitumor Effect of a Calmodulin Antagonist on the Growth of Solid Sarcoma", 180, *Cancer Lett.* 19, 215-220 (1983)) that were proportional to their anti-CaM activity (Hait, W. N., Grais, L., Benz, C., Cadman, E., "Inhibition of Growth of Leukemic Cells by Inhibitors of Calmodulin: Phenothiazines and Melittin", *Cancer Chemother. Pharmocol.*, 14, 202-205 (1985)).

The recent demonstration and elucidation of the phenomenon of multidrug resistance (MDR) has led to the search for drugs that could sensitize highly resistant cancer cells to chemotherapeutic agents. MDR is the process whereby malignant cells become resistant to structurally diverse chemotherapeutic agents following exposure to a single drug (Riordan, J. R., and V. Ling, "Genetic and Biochemical Characterization of Multidrug Resistance", *Pharmol. Ther.*, 28, 51-75 (1985)). MDR cell lines classically have been associated with decreased drug accumulation due to enhanced efflux as well as diminished influx of chemotherapeutic drugs (Inaba M., and R. K. Johnson, "Uptake and Retention of Adriamycin and Daunorubicin by Sensitive and Anthracycline-Resistant Sublines of P388 Leukemia", *Biochem. Pharmacol.*, 27, 2123-2130 (1978) and Fojo, A. S. Akiyama, M. M. Gottesman, and I. Pastan, "Reduced Drug Accumulation in Multiple-Drug Resistant Human KB Carcinoma Cell Lines", *Cancer Res.*, 45, 3002-3007 (1985)). This effect appears to be attributable to the overexpression of a 170,000 dalton membrane glycoprotein (P-glycoprotein) which structurally resembles transport proteins in prokaryotic cells (Chen C., J. E. Chin, K. Ueda, C. P. Clark, I. Pastan, M. M. Gottesman, and I. B. Roninson, "Internal Duplication and Homology with Bacterial Transport Proteins in the mdrl (P-glycoprotein) Gene from Multidrug Resistant Human Cells", *Cell*, 47, 381-389 (1986)) and may function as an energy-dependent, drug efflux pump in mammalian cells (Hamada, H., and T. Tsuruo, "Purification of the 170- to 180-Kilodalton Membrane Glycoprotein Associated with MDR; 170-to 180-Kilodalton Membrane Glycoprotein is an ATPase, *J. Biol. Chem*, 263, 1454-1458 (1988) and Akiyama, S., M. M. Cornwell, M. Kuwano, I. Pastan, and M. M. Gottesman, "Most Drugs that Reverse Multidrug Resistance Inhibit Also Photoaffinity Labeling of P-glycoprotein by a Vinblastine Analog", *Mol. Pharmacol.*, 33, 144-147 (1988)).

PTZs have been shown to be among the group of drugs known to modify MDR (Ganapathi, R., and D. Grabowski, "Enhancement of Sensitivity to Adriamycin in Resistant P388 Leukemia by the Calmodulin Inhibitor Trifluoperazine", *Cancer Res.*, 43, 3696-3699 (1983) and Akiyama, S. N. Shiraishi, Y. Kuratomi, M. Nakagowa, and M. Kuwano, "Circumvention of Multiple-Drug Resistance in Human Cancer Cells by Thioridazine, Trifluoperazine and Chlorpromazine", *J. Natl. Cancer Inst.*, 76: 839-844 (1986)). Although the mechanism by which PTZs and other drugs modulate MDR is not yet clear, it has been suggested that their pharmacological properties may be mediated by the calcium messenger system, since the active compounds are known to inhibit voltage-dependent calcium channels (Fleckenstein, A., "Specific Pharmacology of Calcium in Myocardium, Cardiac Pacemakers, and Vascular Smooth Muscle", *Ann. Rev. Pharmacol. Toxicol.*, 17, 149-166 (1977), CaM and protein kinase C (Mori, T., Y. Takai, R. Minakuchi, B. Yu, and Y. Nishizuka, "Inhibitory Action of Chlorpromazine, Dibucaine, and other Phospholipid-Interacting Drugs on Calcium-activated, Phospholipid-Dependent Protein Kinase", *J. Biol. Chem.*, 255 8378-8380 (1980).

Prozialeck, W. C. and Weiss, B., "Inhibition of Calmodulin by Phenothiazines and Related Drugs: Structure-Activity Relationships", *J. Parmacol. Exp. Ther.*, 222, 509-516 (1982) studied the specific structural features which influence the interaction of a large number of PTZ derivatives with CaM, and showed that varying either the PTZ nucleus or the amino side chain altered activity. Specifically, ring-substitutions that increased hydrophobicity increased potency, while modifications of the type or length of the amino side chain affected potency in a manner unrelated to hydrophobicity. Similarly, studies with N-(6-aminohexyl)-1-naphthalenesulfonamide (W-5) and N-(6-aminohexyl)-5-chloro-1-naphthalenesulfonamide (W-7) (Hidaka, H., M. Asano, and T. Tanaka, "Activity-structure Relationship of Calmodulin Antagonists", *Mol. Pharmacol*, 20, 571–578 (1981)) and a series of 15 derivatives of W-7 (MacNeil, S., M. Griffin., A. M. Cooke, N. J. Pettett, R. A. Dawson, R. Owen, and G. M. Blackburn, "Calmodulin Antagonists of Improved Potency and Specificity for Use in the Study of Calmodulin Biochemistry", *Biochem. Pharmacol.*, 37, 1717–1723 (1988)) demonstrated that both halogenation of the naphthalene ring with chlorine, iodine or cyano groups, and increasing the length of the alkyl side chain from 4 to 12 carbons increased their potency against CaM.

Drug binding studies with synthetic peptides and molecular modeling provided a rationale for the importance of both hydrophobicity and molecular structure for the PTZ-CaM interaction. The induction of alpha-helix formation by the binding of $Ca^{2+}$ to CaM results in two distinct regions, a hydrophobic pocket containing two aromatic phenylalanine residues (Phe 89 and 92) oriented to form a charge transfer complex with the aromatic, tricyclic nucleus of the PTZs, and a hydrophilic region at a distance of one-half helical turn formed by glutamic acid residues (Glu 83,84 and 87), which interact with the positively-charged nitrogen atom of the PTZ side chain (Reid, R. E., "Drug Interactions with Calmodulin: The Binding Site", *J. Thero. Biol.*, 105, 63–76 (1983)).

In Johnston et al, *The Lancet*, Apr. 22, 1978 "Mechanism of the Anti-psychotic Effect in the Treatment of Acute Schizophrenia" pp. 842–851 (1978), a clinical trial of the antipsychotic effects of cis-flupenthixol versus trans-flupenthixol versus placebo showed that while cis-flupenthoxil was a potent neuroleptic (especially for "positive" symptoms), trans-flupenthixol had no activity as an anti-psychotic. Since trans-fluopenthixol is a far less potent dopamine antagonist, and the extrapyramidal side effects associated with antipsychotic therapy are attributed to dopamine receptor binding, trans-flupenthixol lacks these side effects. The apparent lack of anti-psychotic activity or extrapyramidal side effects of trans-flupenthixol make it particularly attractive for use as an anti-multidrug resistance agent, since it is these side effects which have proven problematic in reported trials of phenothiazines plus doxorubicin.

Flupenthixol is disclosed in U.K. Patent 925,538 as having utility as a tranquilizer, ataractic, antiemetic, antihistamine, antispasmodic and general central nervous system depressant. No mention is made of any antitumor activity.

Several thioxanthene derivatives are disclosed in U.K. Patent 863,699 as tranquilizers. Again, no mention of anti-tumor activity is made.

Robin L. Miller, et al, *Journal of Clinical Oncology*, Vol 6, No. 5, May 1988, 880–888 demonstrated the possible effectiveness of trifluperazine (a phenothiazine) in combination with doxorubicin in a Phase I/II trial in clinically resistant cancer in humans. The dose limiting factor in these trials was the extrapyramidal side effects associated with trifluperazine.

SUMMARY OF THE INVENTION

It is an object of the present invention to provide a method to sensitize multidrug resistant cells to antitumor agents.

The above object and other objects, aims and advantages are satisfied by the present invention.

The present invention concerns a method for sensitizing multidrug resistant cells to antitumor agents comprising contacting multidrug resistant cells with an effective amount of a compound of the formula

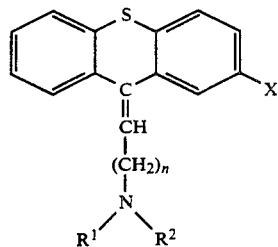

wherein n is 1, 2, 3 or 4, X is selected from the group consisting of $CF_3$, $-O-CF_3$, Br, I, Cl, $C\equiv N$ and $S-CH_3$, and $R^1$ and $R^2$, independent of one another are $-CH_3$, $-CH_2-CH_3$, $CH_2OH$, H, and $CH_2CH_2OH$ or N $R^1R^2$ form a

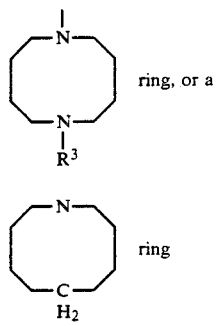

ring, or a ring wherein $R^3$ is $-CH_3$, $-CH_2-CH_3$, $-H$, $CH_3OH-$ and $CH_2CH_2OH$.

X is preferably $CF_3$ and n is preferably 3.

$R^1$ and $R^2$ with the nitrogen atom they are bound to preferably form the following six membered heterocyclic rings:

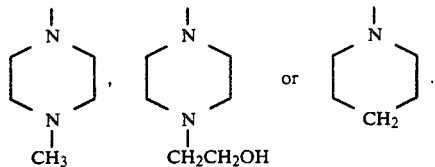

Preferred compounds for use in the present invention are as follows:

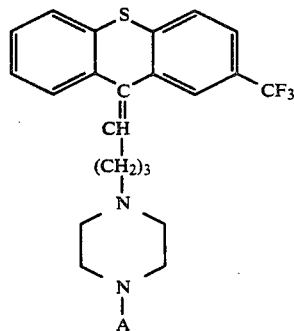

wherein A is $CH_3$ or $CH_2CH_2OH$.

The structural characteristics of such preferred compound include a hydrophobic thioxanthene ring nucleus with a $CF_3$ substitution at position 2, an exocyclic double bond in the trans configuration and a piperazinyl side chain amine with a para-terminal methyl group joined by a 4 carbon alkyl bridge to the ring nucleus.

BRIEF DESCRIPTION OF THE DRAWINGS

FIG. 2 are four graphs (A, B, C and D) which depict the relationship between hydrophobicity and activity of phenothiazine derivatives as antiproliferative and anti-MDR agents. FIG. 2A and FIG. 2B represent the correlation between octanol: buffer partition coefficients, as determined by Prozialcek and Weiss, supra, and the $IC_{50}$'s for inhibition of cell growth ($r = -0.73$, $p = 0.016$) and antagonism of MDR ($r = 0.86$, $p = 0.0015$) for a series of phenothiazine derivatives with ring-substitutions (values from Table 1 hereinbelow).

FIG. 3 are two graphs depicting the relationship between anti-calmodulin activity and antiproliferative or anti-MDR activity for phenothiazine derivatives. FIG. 3A represents the correlation between the $IC_{50}$'s for inhibition of calmodulin-induced activation of phosphodiesterase and the $IC_{50}$'s for inhibition of cell growth ($r = 0.58$, $p = 0.0009$) for 27 phenothiazine derivatives (values from Tables 1-5 hereinbelow). FIG. 3B represents the lack of correlation between the $IC_{50}$'s for inhibition of calmodulin-induced activation of phosphodiesterase and antagonism of MDR ($r = -0.02$, $p = 0.91$) for the same group of phenothiazine derivatives (values from Tables 1-5 hereinbelow).

DETAILED DESCRIPTION OF THE INVENTION

Compounds for use in the present invention having the general formula

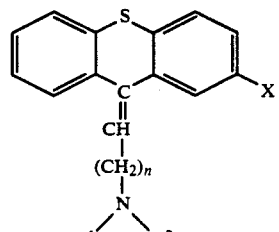

or

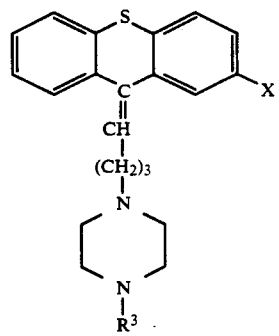

wherein X, $R_3$, $R_1$, $R_2$ and n are preferably as defined below (in order of preference):

| X | $R^3$ | $R^1$ +/or $R^2$ | n |
|---|---|---|---|
| $-CF^3$ | $-CH_3$ | $-CH_2-CH_3$ | 3 |
| $-Cl$ | $-CH_2CH_2OH$ | $-CH_2OH$ | 2 |
| $-O-CH_3$ | $-CH_2CH_3$ | $-CH_3$ | 4 |
| $-Br$ | $-H$ | $-H$ | |
| $-I$ | $CH_2OH$ | $CH_2CH_3OH$ | |
| $-CN$ | | | |
| $-S-CH_3$ | | | |

The results presented herein demonstrate that small changes in the molecular design of the PTZs result in a wide range in their subsequent activity as inhibitors of cell growth and antagonists of MDR, and that these effects appear to be mediated by different mechanisms.

The data presented herein identify certain structural features of the PTZ molecule that affect its activity against cellular proliferative and MDR agents.

Specifically, increasing the hydrophobicity of the PTZ nucleus increased potency against cellular proliferation and against MDR, whereas decreasing the hydrophobicity decreased potency (See Table 1 hereinbelow). Thus, the —CF$_3$ substituted compounds were the most potent drugs, whereas —OH substituted compounds were the least potent drugs. Chlorpromazine sulfoxide, the oxidative metabolite of chlorpromazine, lost most of its antiproliferative effect. However, it retained its effect against MDR, suggesting that first-pass hepatic metabolism of these drugs may not present a major impediment to their clinical use.

The type of amino group also affected potency against MDR but not against cellular proliferation. For example, tertiary amines were more potent than primary or secondary amines, and piperazinyl amines were more potent than non-cyclic groups Moreover, piperazinyl structures that possessed a para-methyl group had consistently greater activity than others (See Table 2 hereinbelow).

The distance between the amino group and the PTZ nucleus was important for both inhibition of cell growth and antagonism of MDR. A four carbon chain was superior to alkyl bridges of shorter lengths (See Table 3 hereinbelow).

Figure 2C:
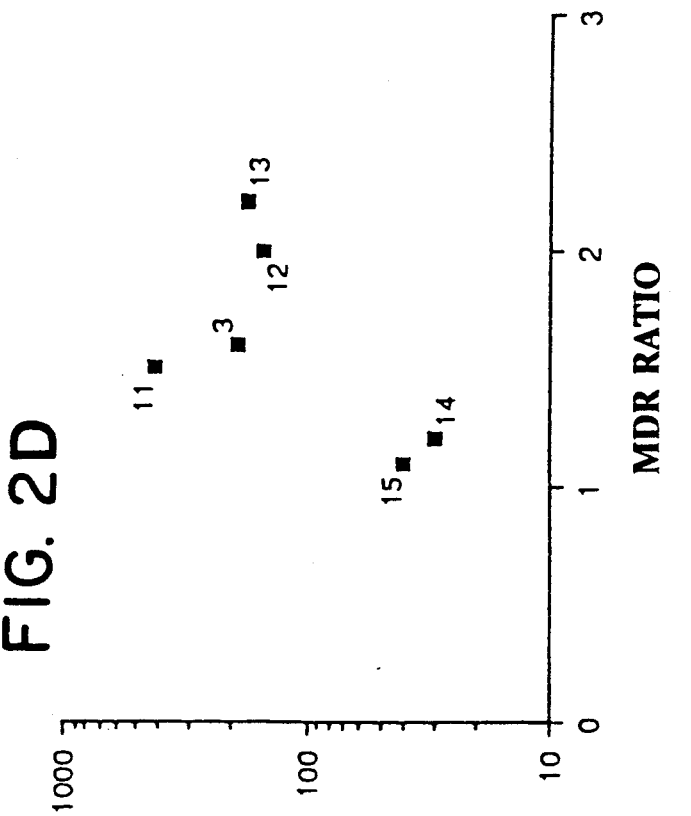
FIG. 2C and FIG. 2D represent the lack of correlation between octanol: buffer partition coefficients and $IC_{50}$'s for inhibition of cell growth ($r = 0.54$, $p = 0.27$) and antagonism of MDR ($r = 0.59$, $p = 0.21$) for a series of 2-Cl substituted phenothiazine derivatives with side chain alterations (values from Tables 2 and 3 hereinbelow). Numbered points represent: (1) promazine, (2) 1-chloropromazine, (3) chlorpromazine, (4) 3-chlorpromazine, (5) 4-chlorpromazine, (6) 7-hydroxychlorpromazine, (7) 3,8-dihydroxychlorpromazine, (8)7,8-dihydroxychlorpromazine, (9) thiomethylpromazine, (10) trifluopromazine, (11)2-chloro-10-[2-(dimethylamino)ethyl]phenothiazine,(12)2-chloro-10-4-(dimethylamino)butyl]-phenothiazine, (13) didesmethylchlorpromazine, (14) desmethylchlorpromazine, and (15) chlorproethazine.
Figure 2D:
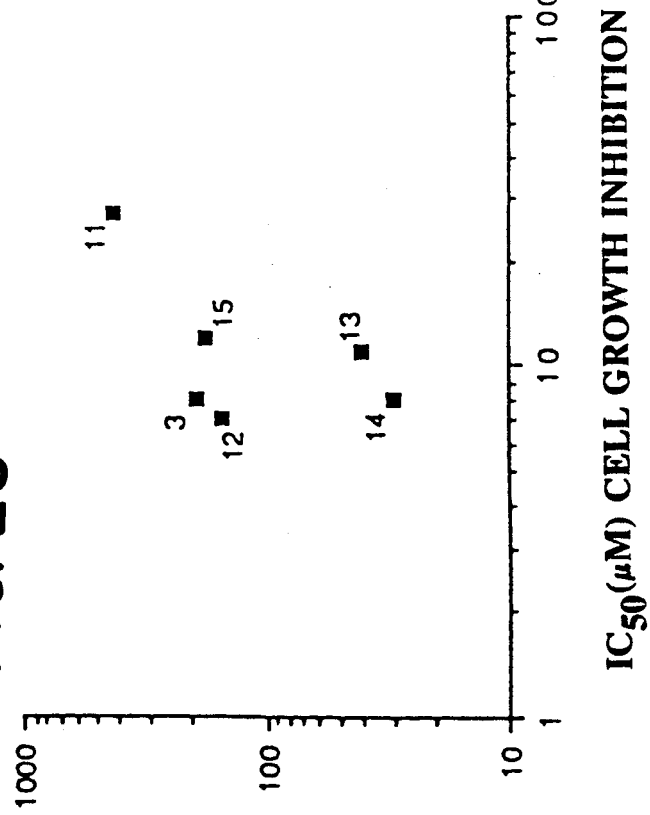

It has been postulated that the effects of PTZs on cells may be due solely to non-specific membrane interactions resulting from their high degree of lipophilicty (Roufogalis, B. D., "Comparative Studies on the Membrane Actions of Depressant Drugs: The Role of Lipophilicity in the Inhibition of Brain Sodium and Potassium-Stimulated ATPase", *J. Neurochem.*, 24, 51–61, (1975)). A careful analysis of the relationship between hydrophobicity and inhibition of cell growth or antagonism of MDR shows that though a correlation exists for ring-substituted PTZ derivatives (FIG. 2A and FIG. 2B), there was no correlation between hydrophobicity and the resultant activity of compounds with specific side chain alterations (FIG. 2C and FIG. 2D). Thus, the degree of lipophilicity of each drug, while important, was not the sole determinant of potency for antiproliferative or anti-MDR activity. The relationship between structure and hydrophobicity of the PTZs and their antiproliferative and anti-MDR activities suggests that in these systems, similar to CaM, the PTZs interact in both a hydrophobic and electrostatic manner with a protein target. Like CaM, it is likely that this target possesses a hydrophobic domain in close proximity to a negatively-charged amino acid.

Although the site of action of PTZs and structurally related compounds for inhibition of cell growth and antagonism of MDR is not yet identified, certain conclusions are suggested from the results herein. The antiproliferative activity of these drugs used individually in the malignant breast cancer cell lines MCF-7 and MCF-7/DOX correlated with their potency as CaM antagonists (FIG. 3A), supporting previous observations with a limited number of PTZs in C$_6$ astrocytoma cells (G. L. Lee and W. N. Hait, "Inhibition of Growth of C$_6$ Astrocytoma Cells by Inhibitors of Calmodulin", *Life Sci.*, 36, 347–354, (1985)), HCT-8 human leukemia cells, L1210 murine leukemia cells, and HCT human colonic carcinoma cells (W. N. Hait and G. L. Lee, *Biochemical Pharmacology*, "Characteristics of the Cytotoxic Effect of the Phenothiazine Class of Calmodulin Antagonists", 34, 3973–3978, (1985)). While these data are consistent with the role of COM in cellular proliferation (Rasmussen and Means, supra), however, the complete lack of correlation between anti-CaM activity and antagonism of MDR points toward an alternative mechanism of inhibition for the pharmacologic reversal of MDR.

Thus, the effect of PTZs in potentiating anthracycline cytotoxicity in MDR cells appears to be clearly distinct from their effect on CaM. This is in contrast to conclusions reached by Ganapathi, R., Grabowski, D., Turinic, R., and Valenzuela, R., "Correlation Between Potency of Calmodulin Inhibitors and Effects on Cellular Levels of Cytoxocity Activity of Doxorubicin (Adriamycin)in Resistant P388 Mouse Leukemia Cells", *Eur. J. Cancer Clin. Oncol.*, 20, 799–806, (1984), who compared the anti-CaM and anti-MDR activity of trifluoperazine, chlorpromazine and prochlorperazine in murine P388/DOX cells. In the context of the much larger sample size of CaM antagonists studied herein, this correlation does not remain significant.

Furthermore, the results herein demonstrate that specific structural features and stereoisomeric configurations are required for optimum activity against MDR, and that these structure-activity relationships differ from those important for the inhibition of CaM. Specifically, while the type of PTZ side chain amine group was not critical to anti-CaM activity (Prozialeck et al, supra) tertiary amines were clearly more potent anti-MDR agents than secondary or primary amines.

The information gained from the results herein allowed for the identification of drugs with certain important features for anti-MDR activity. For example, cis and trans-flupenthixol have a —CF$_3$ substitution at position 2 of the hydrophobic thioxanthene ring, possess a piperazinyl amino side chain, and have a 3 carbon alkyl bridge. While the thioxanthene isomers are more hydrophobic than the PTZs (octanol:buffer partition coefficients (log P) for both flupenthixol isomers=4.25 versus 4.04 for chlorpromazine) (Norman, J. A., and A. H. Drummond, "Inhibition of Calcium-Dependent Regulator-Stimulated Phosphodiesterase Activity by Neuroleptic Drugs is Unrelated to their Clinical Efficacy", *Mol. Pharmacol.*, 16, 1089–1094 (1979)), this alone cannot explain their cellular effects. For example, they are less potent antiproliferative agents than chlorpromazine and other less hydrophobic PTZs. In addition, while the isomers are equally hydrophobic, trans-flupenthixol is a 3-fold more potent anti-MDR agent (FIG. 3) and both isomers are more potent than agents with greater hydrophobicity, such as pimozide (log P=4.88). The orientation of the side chain amine in relation to the tricyclic nucleus appeared to be an important determinant for anti-MDR activity, but not of antiproliferative activity. For example, the trans-thioxanthene isomer displayed greater activity than the cis-isomer against MDR (See Table 5 hereinbelow). Also, studies of the anti-CaM effect of the thioxanthene stereoisomers revealed no difference between cis and trans-flupenthixol (Norman J. A., and A. H. Drummond, supra).

A trivial explanation of the differences in activity observed for the thioxanthene stereoisomers would be differences in their cellular accumulation, however, it is also shown herein that MDR cells accumulate cis and trans-flupenthixol in an equivalent, dose-dependent fashion, in agreement with their nearly identical IC$_{50}$'s for inhibition of cell growth. This suggests that the difference in anti-MDR activity between these stereoisomeric thioxanthenes is due to selective differences in their ability to interact with a unique cellular target, rather than differences in their intracellular accumulation.

Figure 5:
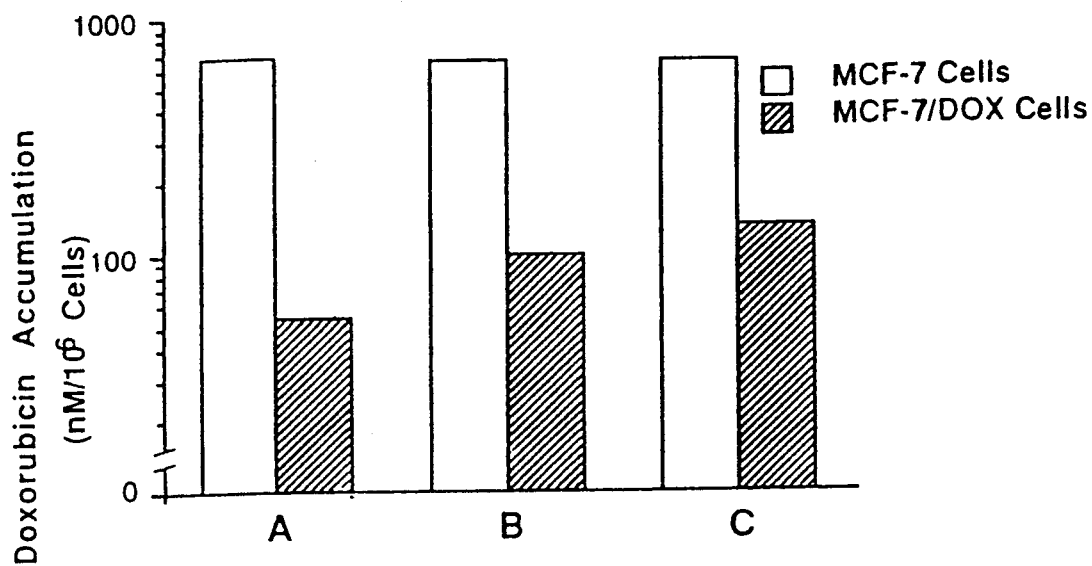
FIG. 5 is a series of bar graphs depicting the effect of thioxanthene isomers on the accumulation of doxorubicin in sensitive MCF-7 and MDR MCF-7/DOX cells. Cells were incubated for 3 hours with 15 $\mu M$ doxorubicin in the absence (A) or presence of 3 $\mu M$ cis-flupenthixol(B) or 6 $\mu M$ trans-flupenthixol(C). Cell associated doxorubicin was determined spectra-fluorometrically. Values are means from duplicate determinations.

While the antiproliferative effects of the PTZs and related compounds were approximately equipotent in both the MCF-7 and the MCF-7/DOX malignant cell lines, the ability of these drugs to potentiate the effect of doxorubicin (See Table 5 hereinbelow) as well as their ability to increase the cellular accumulation of doxorubicin (FIG. 5 occurred only in the MDR cell line, suggesting that the latter effects were mediated through a target(s) overexpressed in MDR cells. One logical site would be the putative drug efflux pump, P-glycoprotein, the gene product encoded for by the recently cloned mdrl gene (Chen et al, supra, Gros, P., Y. Ben Neriah, J. M. Croop, and D. E. Housman, "Isolation and Expression of a cDNA (mdr) that Confers Multidrug Resistance", Nature, 323, 728-731 (1986); and Ueda K., C. Cardarelli, M. M. Gottesman, and I. Pastan, "Expression of a Full-length cDNA for the Human mdrl Gene Confers Resistance to Colchicine, Doxorubicin, and Vinblastine", Proc. Natl. Acad. Sci. USA, 84, 3004-3008 (1987)). A current hypothesis regarding the mechanism by which MDR cells reduce cellular accumulation of anthracyclines is through increased expression of this plasma membrane glycoprotein in MDR cells (Riordan and Ling, supra) and that compounds which antagonize MDR compete with cytotoxic drugs for specific drug binding sites on the protein (Cornwell, M. M., I. Pastan, and M. M. Gottesman, "Certain Calcium Channel Blockers Bind Specifically to Multidrug Resistant Human KB Carcinoma Membrane Vesicles and Inhibit Drug Binding to P-glycoprotein", J. Biol. Chem., 262, 2166-2170) (1978). Though calcium channel blockers can inhibit binding of a photoaffinity labelled vinblastine analog to P-glycoprotein, phenothiazines were far less effective (Akiyama et al, supra). However, the failure of PTZs to block vinblastine binding to the mdrl gene product does not rule out the interaction with other sites on the protein. For example, Hamada and Tsuruo have recently demonstrated ATPase activity of the molecule (Hamada and Tsuruo, supra). Since the ATP binding site is at a different location than the putative drug binding region, and since PTZs are known to inhibit other ATPases (Pang and Briggs, supra and Raess, B. U., and F. F. Vincenzi, "Calmodulin Activation of Red Blood Cells ($Ca^{2+}+Mg^{2+}$)-ATPase and Its Antagonism by Phenothiazines", Mol. Pharmacol., 18, 253-258 (1980)), it is possible that they interfere with this aspect of P-glycoprotein's proposed function. Alternatively, Center (Center, M. C., "Mechanisms Regulating Cell Resistance to Adriamycin", Biochem. Pharmacol., 34, 1471-1476 (1985)) demonstrated that trifluoperazine increased phosphorylation of this protein in MDR Chinese hamster lung cells and enhanced doxorubicin accumulation and cytotoxicity, suggesting the PTZs may indirectly affect P-glycoprotein. Finally, the lack of direct correlation between the increase in doxorubicin accumulation and increase in sensitivity of MCF-7/DOX cells in the examples herein (FIG. 5) suggests that the thioxanthenes may exert their effect through more than one mechanism.

Several groups have suggested that protein kinase C may play an important role in MDR (Ido, M., T. Asao, M. Sakurai, M. Inagaki, M. Saito, and H. Hidaka, "An Inhibitor of Protein Kinase C, 1-(5-isoquinolinylsulfonyl)-2-methylpiperazine (H-7) Inhibits TPA-induced Reduction of Vincristine Uptake from P388 Murine Leukemic Cell", Leukemia Res, 10, 1063-1069 (1986) and Ferguson, P. F., and Y. Cheng, "Transient Protection of Cultured Human Cells Against Antitumor Agents by 12-O-tetradecanoylphorbol-13-acetate", Cancer Res., 47, 433-441 (1987)). Drugs that stimulated PKC, such as the phorbol esters, produce increased levels of anthracycline resistance in MCF-7/DOX cells, and induce a MDR-like phenotype in sensitive MCF-7 cells (Fine, R. L., J. Patel, and B. A. Chabner, "Phorbol Esters Induce Multidrug Resistance in Human Breast Cancer Cells", Proc. Natl. Acad. Sci. USA, 85, 582-586 (1988)). These effects were reversed by trifluoperazine at concentrations similar to those used in the present study. Furthermore, the MCF-7/DOX cell line had up to a 15-fold increased level of PKC activity compared to the parental MCF-7 cells (Fine et al, supra and Palayoor, S. T., J. M. Stein, and W. N. Hait, "Inhibition of Protein Kinase C by Antineoplastic Agents: Implications for Drug Resistance", Biochem. Biophys. Res. Commun., 148, 718-725 (1987)). Results from studies utilizing the isoquinolinesulfonamide derivative, H-7, a relatively specific PKC inhibitor, were ambiguous with regard to the possible anti-MDR effect of inhibiting PKC. While some reported that H-7 failed to sensitize L1210/DOX cells (Ganapathi, R., and D. Grabowski, "Differential Effect of the Calmodulin Inhibitor Trifluoperazine in Modulating Cellular Accumulation, Retention and Cytoxicity of Doxorubicin in Progressively Doxorubicin-Resistant L1210 Mouse Leukemia Cells", Biochem. Pharmacol., 37, 185-193 (1988)), others found that it does sensitize $KC/ADR_{10}$ human breast cells (Ahn, C.-H., R. L. Fine, and W. B. Anderson, "Possible Involvement of Protein Kinase C in the Modulation of Multidrug Resistance", Proc. Am. Assoc. Cancer Res., 29, 1182(1988)). When studied in isolated systems, the concentrations of PTZs required to inhibit PKC (Schatzman, R. C., B. C. Wise, and J. F. Kuo, "Phospholipid-sensitive Calcium-Dependent Protein Kinase: Inhibition by Anti-Psychotic Drugs", Biochem. Biophys. Res. Commun., 98, 669-676 (1981)) are many fold higher than those which were found sufficient to antagonize MDR. For example, the $IC_{50}$'s for inhibition of PKC by trifluoperazine, chlorpromazine and fluphenazine were 10 to 50-fold greater than those found to antagonize MDR (See Table 4 hereinbelow). The thioxanthenes are particularly poor inhibitors of PKC, having $IC_{50}$'s of 335 to more than 1000 $\mu M$ (Scatzman, R. C., B. C. Wise, and J. F. Kuo, supra.) whereas concentrations of 3.5 to 10 $\mu M$ trans-flupenthixol caused a 15 to 37-fold antagonism of MDR. Thus, while the activation and inhibition of PKC offers an attractive hypothesis for the modulation of MDR, it appears that the anti-MDR effects of the PTZs and thioxanthenes are not likely to be mediated solely through this enzyme.

Specific structure-activity relationships for PTZs and thioxanthenes as antiproliferative agents in malignant cells, and as antagonists of MDR in a human breast cancer cell line has been demonstrated herein, suggesting ideal structures for more potent and less toxic compounds. Inhibition of CaM has been shown herein to correlate with the antiproliferative effect of PTZs but a lack of correlation between CaM antagonism and anti-MDR activity has been found, suggesting that the ability of these drugs to reverse MDR is not through interactions with CaM, but through another, as yet unidentified cellular target. Furthermore, it has been shown herein the effect of PTZs in sensitizing cells to doxorubicin to occur only in MDR cells, implying that this target is overexpressed in cells of this phenotype. Finally, these structure-activity relationships have been used to identify a thioxanthene stereoisomer, trans-flupenthixol, which possesses greater activity against MDR in vitro than the previously believed most effective PTZ, trifluoperazine.

Trans-flupenthixol may prove to be particularly suited for clinical use against MDR tumors. Clinical trials of the antipsychotic effects of flupenthixol in humans showed that while cis-flupenthixol was far more effective than trans-flupenthixol, the latter was far less toxic (Johnston, E. C., T. J. Crew, C. D. Frith, M. W. D. Carney and J. S. Price, supra). This observation may be explained by biochemical and crystallographic evidence that cis-flupenthixol is a powerful antagonist of dopamine receptors (Huff, R. M. and B. Molinoff, "Assay of Dopamine Receptors With [alpha-$^3$H]Flupenthixol", *J. Pharmacol. Exp. Ther.*, 232, 57–61 (1984) and Post, M. L., U. Kennard, A. S. Horn, "Stereoselective Blockade of the Dopamine Receptor and the X-ray Structures of Alpha and Beta-flupenthoxil", *Nature*, 256, 342–343 (1975)), whereas trans-flupenthixol, which displays the greater potency against MDR, has virtually no activity as a dopamine antagonist. This lack of anti-dopaminergic activity may explain the apparent lack of extrapyramidal side effects seen with this agent (Nielsen, I. M., V. Pedersen, M. Nymark, K. F. Franck, V. Boeck, B. Fjalland, and A. V. Christensen, "Comparative Pharmacology of Flupenthixol and Some Reference Neuroleptics", *Acta.-Pharmacol. Toxicol. (Copenh).*, 33, 353–362 (1973)). Extrapyramidal side effects have proven to be dose limiting in Phase I trials that combined trifluoperazine with bleomycine (Hait, W. N., J. S. Lazo, D.-L. Chen, and V. Gallicchio, "Preclinical and Phase I-II Studies of Bleomycin (BLEO) With Calmodulin-Antagonist (CaM-A)", *Proc. Am. Assoc. Cancer Res.*, 26, 1283 (1985)) or doxorubicin (Miller, R. L., R. M. Bukowski, G. T. Budd, J. Purvis, J. K. Weick K. Shepard, K. K. Midha, and R. Ganapathi, supra).

The invention will now be described with reference to the following non-limiting examples.

EXAMPLES

Example 1

Cell Lines and Culture

MCF-7 human breast cancer cells, and the multidrug resistant subclone MCF-7/DOX selected by stepwise exposure of parental cells to increasing concentrations doxorubicin, were maintained in exponential growth in 75 cm$^2$ culture flasks RPMI 1640 medium supplemented with 5% fetal bovine serum in a humidified atmosphere of 5% $CO_2$ and 95% air. MCF-7/DOX cells were approximately 200-fold more resistant to doxorubicin than the parental cell line, and maintained a stable MDR phenotype while grown in drug free medium for a period of at least 3 months. Cell lines were routinely tested and found to be free of contamination by mycoplasma or fungi.

Example 2

Effect on Drugs on Cell Growth and MDR

Cells in exponential growth were trypsinized (0.5% trypsin in phosphate-buffered saline), disaggregated into single cell suspensions, counted electronically (Coulter, Hialeah, Fla.), and dispensed in 100 μl volumes into 96-well microtiter plates with a multichannel pipet (Flow Labs, Titertek) at a concentration of 0.5–1.0×10$^4$ cells per well. Cells were allowed to attach to the plastic and to resume growth for 24 hours prior to the addition of 100 μl of drug-containing medium. Drugs were dissolved in small amounts of sterile water or 1% DMSO (final culture concentration<0.05% DMSO) before dilution with medium. Controls were exposed to vehicle-containing medium.

Following a 48 hour incubation at 37° C., the supernatants of each well were gently aspirated, and cells were fixed and stained with 100 μl of 0.5% methylene blue (Sigma) in 50% ethanol (w/v) for 30 minutes at room temperature, as described in Finlay, G. J., B. C. Baguley, and W. R. Wilson, "A Semiautomated Microculture Method for Investigating Exponentially Growing Carcinoma Cells", *Anal. Biochem*, 139, 272–277 (1984).

Unbound stain was removed by decanting and subsequent emersion in three, one-liter washes of distilled, deionized water. The plates were dried for 12 hours and stained protein solubilized with 200 μl of sodium N-lauroyl sarcosine (Fluka, Switzerland) solution (1% v/v in PBS). The optical density of each well was determined by absorbence spectrophotometry at a wavelength of 600 nm, using a microculture plate reader (Titertek Multiscan MCC/340) interfaced to an Apple IIe computer. Inhibition of cell growth was expressed as a percentage of absorbance of drug-free control culture.

Figure 1:
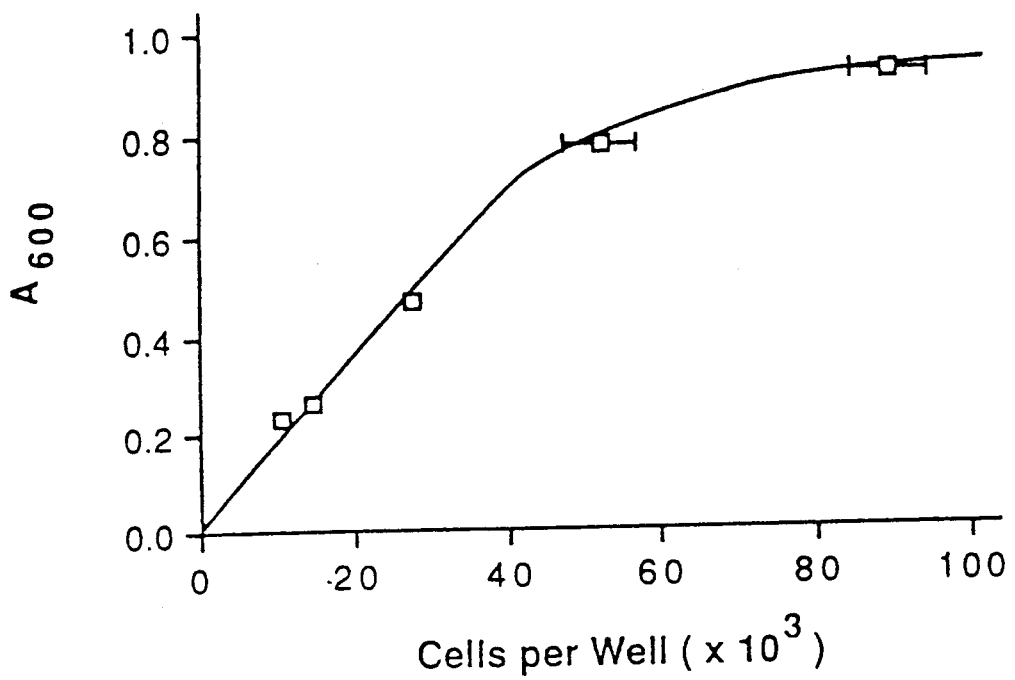
FIG. 1 is a graph depicting the correlation between absorbance ($A_{600}$) of stained cellular protein and cell count. Each point represents the mean of quadruplicate determinations. Bars represent the standard error when greater than the symbol.
Figure 4:
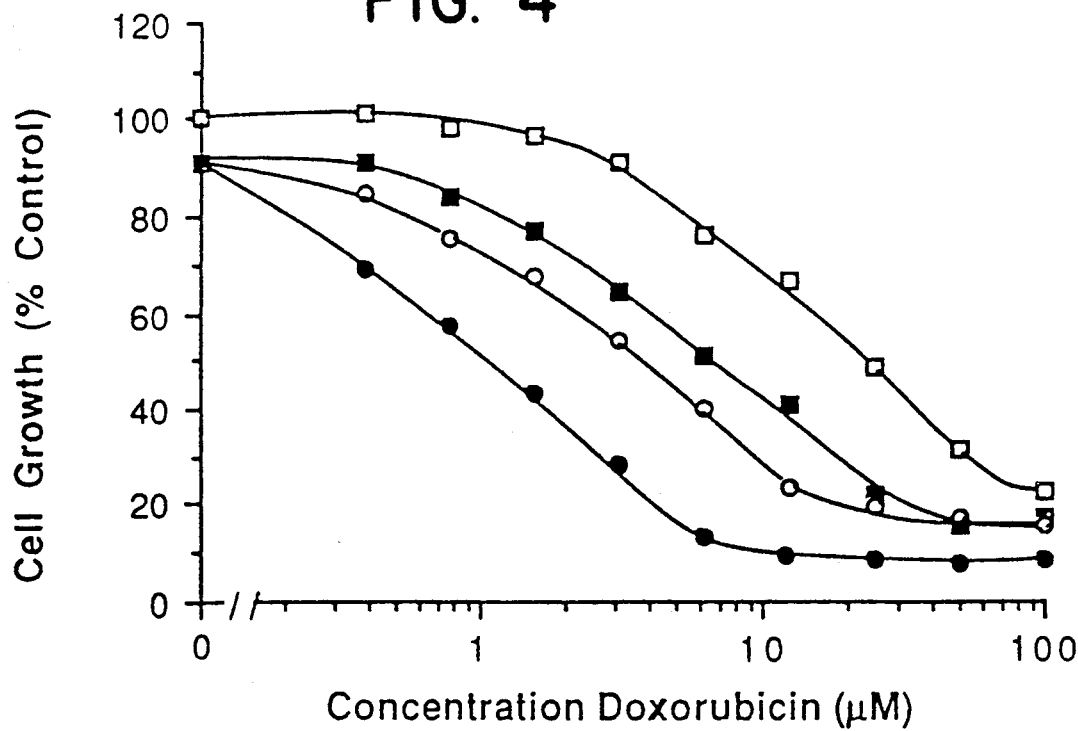
FIG. 4 is a graph depicting the effect on the sensitivity of MDR cells to doxorubicin by phenothiazines and structurally related modifiers. MCF-7/DOX cells (MCF-7 is a human breast cancer cell line and MCF-7/DOX is its multidrug resistant subclone) were exposed to 0-100 $\mu M$ doxorubicin for 48 hours in the absence (□) or presence of fluphenazine (■), cis-flupenthixol(o), or trans-flupenthixol (●) at concentrations that alone produced 10% inhibition of cell growth. Cell growth was determined by a microtiter assay.

To determine the optimal conditions for this assay, plates were innoculated in duplicate with various initial cell concentrations. One half plate was assayed daily for five consecutive days by standard trypsinazation and electronic counting, while the other half of each plate was stained as described above. FIG. 1 demonstrates the linear correlation between $A_{600}$ from stained wells and actual cell number for the MCF-7/DOX cell line with final cell concentrations between 0–50,000 cells per well. (MCF-7/DOX cells were grown in 96-well microtiter plates at initial concentrations of 10,000 cells/well and enumerated after 24, 48, 72, 96 and 110 hours incubations by either absorbance spectrophotometry or with a Coulter Counter). Similar results were obtained for the sensitive cell line. Final assay conditions were chosen to ensure that optical density measurements fell on the linear portion of this curve. This screening system has proven extremely reproducible, with less than 5% variability between IC$_{50}$ values from dose-response curves to doxorubicin from different experiments run on different days.

The effect of PTZs or related drug alone on cell growth was examined by exposing cells to 0–100 μM drug as described above with each condition repeated in quadruplicate. IC$_{50}$ was the concentration of drug that reduced staining (A$_{600}$) of 50% of vehicle treated controls. Final IC$_{50}$ values represent the average of between 3 and 5 separate experiments which differed by less than 10%.

The effect of PTZs on MDR was studied by exposing cells to 0–100 μM doxorubicin in the absence or presence of a concentration of a PTZ derivative that alone produced 10% inhibition of cell growth. Dose-response curves were corrected for the 10% inhibition of cell growth caused by the PTZs alone. The MDR Ratio was defined as the ratio of the IC$_{50}$ doxorubicin alone divided by the IC$_{50}$ for doxorubicin in the presence of modifier. This ratio represents the increase in apparent potency of doxorubicin produced cell by each PTZ derivative. MDR Ratio=IC$_{50}$ alone÷IC$_{50}$ DOX+drug.

Example 3

Isobologram Analysis

After determining the $IC_{50}$ concentrations for doxorubicin and individual MDR modifiers in MCF-7/DOX cells, a series of dose-response curves to a single modifier in the presence of fixed concentrations of doxorubicin were determined by the microtiter assay system described above. The concentration of doxorubicin plus modifier that together resulted in 50% inhibition of MCF-7/DOX cell growth were plotted and the $IC_{50}$ isobole compared to the predicted line of additivity, using criteria described in Berenbaum, M. C., "Criteria for Analyzing Interactions Between Biologically Active Agents", *Adv. Ca. Res.*, 35, 269–335, (1981).

Example 4

Cellular Accumulation of Derivatives

Duplicate aliquots of $3 \times 10^6$ MCF-7/DOX cells in a total volume of 2 ml were incubated at 37° C. for 3 hours in the presence of 0–100 μM of each drug. Cells were washed three times in cold PBS by centrifugation at 100× g for 10 minutes, resuspended in 2 ml of 0.3N HCl in 50% ethanol, and sonicated for 10 pulses at 200 ws with a Tekmar cell sonicator (Tekmar, Cincinnati, Ohio). Following centrifugation at 1000× g for 30 minutes, the supernatant was removed and assayed for drug content with a Perkin-Elmer 512 spectrofluorometer (Norwalk, Conn.). Optimal excitation and emission wavelengths for both thioxanthene isomers were determined to be 320 nm and 400 nm, respectively. Cellular drug content (nM/$10^6$ cells) was computed from standard curves prepared with known amounts of drug in 0.3N HCl in 50% ethanol.

Example 5

Cellular Accumulation of Doxorubicin

Duplicate aliquots of $3 \times 10^6$ MCF-7 or MCF-7/DOX cells in a total volume of 2 ml were incubated at 37° C. for 3 hours with 15 μM, 1/5μM or 0.15 μM doxorubicin in the absence or presence of either 3 μM cis-flupenthixol or 6 μM trans-flupenthixol (concentrations which alone produce 10% inhibition of cell growth). Cells were washed in cold PBS, extracted with 0.3N HCl in 50% ethanol, sonicated and centrifuged as described above. Supernatants were removed and assayed fluorometrically for doxorubicin content using excitation and emission wavelengths of 470 nm and 585 nm, respectively, as described in Ganapathi et al., supra. Cellular content of doxorubicin was computed from standard curves prepared with known amounts of doxorubicin. The presence of thioxanthene isomers was shown not to effect the spectrofluometric activity of doxorubicin.

Example 6

Drugs

Doxorubicin, obtained by Adria Labs was freshly prepared in distilled water for each experiment. Phenothiazine derivatives and related drugs were obtained as follows: chlorpromazine hydrochloride, trifluoperazine dihydrochloride, chlorpromazine sulfoxide hydrochloride, 2-chloro-10-[2-(dimethylamino)ethyl]phenothiazine hydrochloride, 2-chloro-10-[4-(dimethylamino)-butyl]phenothiazine hydrochloride, promazine hydrochloride, trifluopromazine hydrochloride, 2-thiomethylpromazine hydrochloride, 1-chloropromazine hydrochloride, 3-chloropromazine hydrochloride, 4-chloropromazine hydrochloride and prochlororperazine ethanesdisulfonate from Smith Kline and French Laboratories (Philadelphia, Pa.); 7-hydroxychlorpromazine, 3,8-dihydroxychlorpromazine, 7,8-dihydroxychlorpromazine, desmethylchlorpromazine hydrochloride and didesmethylchlorpromazine hydrochloride from the National Institute of Mental Health (Bethesda, Md.); promethazine hydrochloride from Wyeth Laboratories (Radnor, Pa.); chlorproethazine hydrochloride from Rhone-Poulenc (Paris, France); imipramine hydrochloride and 2-chloroimipramine hydrochloride from Geigy Pharmaceuticals (Summit, N.J.); haloperidol, pimozide, penfluridol and 4-(4-chloro,α,α,α-trifluoro-m-tolyl-1-[4,4-bis(p-flourophenyl)butyl]-4-piperidinol (R-6033) from Janssen Pharmaceutica (Beerse, Belgium); quinacrine dihydrochloride from Sterling-Winthrop Research Institute (Renssalear, N.Y.); fluphenazine from E. R. Squibb and Sons; cis and trans-flupenthixol from H. Lundbeck (Copenhagen, Denmark); and perphenazine from Sigma (St. Louis, Mo.).

Example 7

Effect of Modifying the Phenothiazine Nucleus on Cell Growth and MDR

Table 1 shows the structures, $IC_{50}$ values for cell growth inhibition and MDR Ratios for a series of promazine derivatives having different substitutents on the PTZ nucleus.

TABLE 1

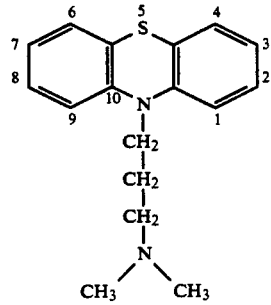

| Substituent | Position | Name | Cell Growth Inhibition $IC_{50}$ (μM) | MDR Ratio |
|---|---|---|---|---|
| | | Promazine | 26 | 1.2 |

TABLE 1-continued

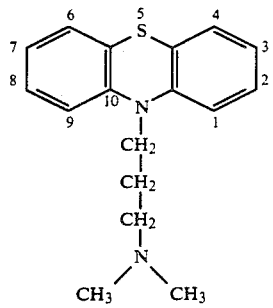

| Substituent | Position | Name | Cell Growth Inhibition IC$_{50}$ (μM) | MDR Ratio |
|---|---|---|---|---|
| —Cl | 1 | 1-Chlorpromazine | 21 | 1.3 |
| —Cl | 2 | Chlorpromazine | 8 | 1.6 |
| —Cl | 3 | 3-Chlorpromazine | 10 | 1.3 |
| —Cl | 4 | 4-Chlorpromazine | 15 | 1.4 |
| —Cl; —OH | 2; 7 | 7-Hydroxychlorpromazine | 50 | 1.0 |
| —Cl; —OH; —OH | 2; 3; 8 | 3,8-Dihydroxychlorpromazine | 400 | 0.9 |
| —Cl; —OH; —OH | 2; 7; 8 | 7,8-Dihydroxychlorpromazine | 63 | 0.8 |
| —S—CH$_3$ | 2 | Thiomethylpromazine | 20 | 1.5 |
| —CF$_3$ | 2 | Trifluopromazine | 16 | 2.0 |
| =O | 5 | Chlorpromazine Sulfoxide | 500 | 2.2 |

Inhibition of cell growth was determined by exposing MCF-7/DOX cells to 0–100 μM of each PTZ derivative. IC$_{50}$ is the concentration that produced 50% inhibition of cell growth as measured by a microtiter assay system described in methods. To determine the MDR Ratio, MCF-7/DOX cells were exposed to 0–100 μM doxorubicin in the presence or absence of phenothiazine at a concentration which alone produced 10% inhibition of cellular growth. MDR Ratio is the IC$_{50}$ for doxorubicine alone divided by the IC$_{50}$ doxorubicin in the presence of phenothiazine. All values represent the mean of at least two separate experiments having less than 5% variation between them; each experiment was run in quadruplicate (this also holds true for Tables 2, 3 and 5 hereinbelow).

The unsubstituted PTZ, promazine, inhibited cell growth (IC$_{50}$=26 μM), and sensitized MCF-7/DOX cells to doxorubicin by only 20% (MDR Ratio=1.2). However, substitution of a chlorine at positions 1, 2, 3 or 4 increased potency against cell growth by up to 3-fold, with the most potent compound (chlorpromazine) having a chlorine at position 2 (IC$_{50}$=8 μM). Substituting the chlorine moiety at position 2 also had the greatest effect against MDR, with chlorpromazine sensitizing resistant cells to doxorubicin by 60% (MDR Ratio=1.6). Similarly, substitution at position 2 with a CF$_3$ group also increased potency against cell growth and MDR. Accordingly, trifluopromazine was 1.6-fold more potent than promazine in inhibiting cell growth (IC$_{50}$=16 μM), and was 67% more potent against MDR (MDR Ratio=2.0). Conversely, adding an —OH group decreased the potency of both effects. For example, 7-hydroxychlorpromazine was 6-fold less potent than chlorpromazine in inhibiting cell growth, while the dihydroxylated analogs 7,8 and 3,8 dihydroxychlorpromazine were up to 50-fold less potent as cell growth inhibitors, with IC$_{50}$'s of 63 uM and 400 μM, respectively. In addition, the hydroxylated analogs had no activity against MDR, and further increased resistance to doxorubicin (MDR Ratios<1.0). Oxidation of the bridge sulfur to produce chlorpromazine sulfoxide markedly reduced antiproliferative activity (IC$_{50}$=500 μM), but increased activity against MDR (MDR Ratio=2.2).

Example 8

Effect of Modifying the Side Chain Amino Group on Cell Growth and MDR

To determine the structural importance of the side chain amino group, PTZs possessing different types of amino groups and side chains of varying lengths were studied. Table 2 hereinbelow shows that PTZs containing tertiary amines (chlorpromazine and chlorproethazine), secondary amines (desmethylchlorpromazine), and primary amines (didesmethylchlorpromazine) possess similar activity in inhibiting cell growth (IC$_{50}$'s=-8–12 μM). However, PTZs having tertiary amines were clearly more potent antagonists of MDR than those with secondary or primary amines, producing a 1.6 to 2.2-fold increase in sensitivity to doxorubicin in MDR cells.

TABLE 2

[Phenothiazine structure with positions 1-10, N at position 10 bearing —CH$_2$—CH$_2$—CH$_2$—R side chain, and X substituent at position 2]

| X | R | Name | Cell Growth Inhibition IC 50 ($\mu$M) | MDR Ratio |
|---|---|---|---|---|
| —Cl | —NH | Didesmethylchlorpromazine | 11 | 1.1 |
| —Cl | —NH—CH$_3$ | Desmethylchlorpromazine | 8 | 1.2 |
| —Cl | —N(CH$_3$)$_2$ | Chlorpromazine | 8 | 1.6 |
| —Cl | —N(CH$_2$—CH$_3$)$_2$ | Chlorproethazine | 12 | 2.2 |
| —Cl | —N(piperazinyl)N—CH$_2$—CH$_2$—OH | Perphenazine | 32 | 2.0 |
| —Cl | —N N—CH$_3$ (piperazinyl) | Prochlorperazine | 22 | 2.6 |
| —CF$_3$ | —N(CH$_3$)$_2$ | Trifluopromazine | 14 | 2.0 |
| —CF$_3$ | —N(piperazinyl)N—CH$_2$—CH$_2$—OH | Fluphenazine | 33 | 2.5 |
| —CF$_3$ | —N N—CH$_3$ (piperazinyl) | Trifluoperzine | 19 | 3.1 |

For example, the IC$_{50}$'s of chlorpromazine and desmethylchlorpromazine were equal (8 $\mu$M), whereas chlorpromazine was more potent than desmethylchlorpromazine against MDR (MDR ratios=1.6 and 1.2, respectively). Other changes in the type of amino group also affected anti-MDR activity. For example, piperazinyl derivatives increased potency against MDR. Accordingly, the MDR ratios for trifluoperazine (3.1) and fluphenazine (2.5), compounds with piperazinyl amino side chains, were greater than that of trifluopromazine (2.0), a compound with an identical hydrophobic ring-substitution, but possessing an aliphatic side chain. Similarly, perphenazine and prochlorperazine (MDR ratios=2.0 and 2.6) were more potent antagonists of MDR than chlorpromazine (MDR ratio=1.6). This series also points out the importance of the —CF$_3$ substitution at position 2 for anti-MDR activity. For example, the MDR Ratio for trifluoperazine (3.1) was greater than that of prochlorperazine (2.6). These PTZs have identical structures except that the former has a —CF$_3$ instead of a —Cl at position 2. A similar relationship is seen by comparing fluphenazine (2.5) to perphenazine (2.0), also identical molecules except for the —CF$_3$ ring substitution. Finally, a para-methyl substitution on the piperazine appeared more potent than an ethanol group for anti-MDR activity of compounds, as seen by comparing the MDR ratios for prochlorperazine (2.6) to perphenazine (2.0), or trifluoperazine (3.1) to fluphenazine (2.5).

Table 3 hereinbelow shows the effect on cell growth and MDR of a series of 10-[alkyl-dimethylamino]phenothiazines in which the length of the amino-containing side chain was varied. As can be seen, moving from a two to a four carbon alkyl bridge increased the antiproliferative and anti-MDR effects of these compounds. For example, 2-chloro-10-[4-(dimethylamino)butyl]-phenothiazine, which as a four carbon chain separating the amino group from the PTZ nucelus, was a more potent antiproliferative agent (IC$_{50}$=7 uM) and anti-MDR agent (MDR Ratio=2.0) than any of the other four compounds with two or three carbon alkyl chains. Conversely, promethazine, which has an isopropyl side chain was a less potent inhibitor of cell growth than promazine, which has a three carbon chain.

Example 10

Correlation Between Anti-calmodulin Activity and Inhibition of Cellular Proliferation and MDR

TABLE 3

[Phenothiazine structure with positions 1-10, S at top, N at position 10 with R substituent, and X at position 2]

| X | R | Name | Cell Growth Inhibition IC$_{50}$ ($\mu$M) | MDR Ratio |
|---|---|---|---|---|
| —Cl | —CH$_2$—CH$_2$—N(CH$_3$)$_2$ | 2-Chloro-10-[2-(dimethylamino)ethyl] phenothiazine | 27 | 1.5 |
| —Cl | —CH$_2$—CH$_2$—CH$_2$—N(CH$_3$)$_2$ | Chlorpromazine | 8 | 1.6 |
| —Cl | —CH$_2$—CH$_2$—CH$_2$—CH$_2$—N(CH$_3$)$_2$ | 2-Chloro-10-[4-(dimethylamino)butyl] phenothiazine | 7 | 2.0 |
| —H | —CH$_2$—CH(CH$_3$)—N(CH$_3$)$_2$ | Promethazine | 29 | 1.9 |
| —H | —CH$_2$—CH$_2$—CH$_2$—N(CH$_3$)$_2$ | Promazine | 27 | 1.2 |

Example 9

Influence of Hydrophobicity of Phenothiazines on Cellular Proliferation and MDR

To determine the influence of hydrophobicity on the effect of PTZs on cellular proliferation and MDR, the octanol: buffer partition coefficients for each of the 10 ring-substituted promazine derivatives as determined by Proziolack and Weiss, supra were compared to the IC$_{50}$'s for inhibition of cell growth and to the MDR Ratios. FIGS. 1A and B demonstrate the excellent correlation between hydrophobicity and both antiproliferative activity (r=−0.73, p=0.016) and MDR antagonism (r=0.86, p=0.0015).

To determine if the differences in potency of compounds with side chain alterations were also due to changes in overall hydrophobicity, the octanol: buffer partition coefficients for each of the drugs in Tables 2 and 3 that had —Cl substitutions at position 2 of the PTZ ring were compared to their IC$_{50}$'s for inhibition of cell growth and to their MDR Rations (FIGS. 1C and D). In contrast to the results for ring-substituted PTZs, no statistically significant correlation was found between hydrophobicity and potency of compounds with side chain alterations for inhibition of cell growth (r=0.54, p=0.27) or antagonism of MDR (r=0.59, p=0.21).

To examine the role of CaM as a possible target for the effect of PTZs on cellular proliferation and MDR, the IC$_{50}$'s for the inhibition of CaM by each of the PTZs and structurally related compounds (Table 4) were compared to their potency as inhibitors of cell growth and their effect on MDR. FIGS. 2A and B show a good correlation between anti-CaM activity and antiproliferative activity (r=0.58, p=0.0009), whereas no correlation was found between anti-CaM activity and effect on MDR (r=−0.02, p=0.91).

TABLE 4

| Compound | Calmodulin IC$_{50}$ ($\mu$M) |
|---|---|
| Promazine | 110 |
| 1-Chlorpromazine | 74 |
| Chlorpromazine | 40 |
| 3-Chlorpromazine | 24 |
| 4-Chlorpromazine | 25 |
| 7-Hydroxychlorpormazine | 68 |
| 3,8-Dihydroxychlorpromazine | 183 |
| 7,8-Dihydroxychlorpromazine | 82 |
| Thiomethylpromazine | 42 |
| Trifluopromazine | 28 |
| Chlorpromazine sulfoxide | 2200 |
| Didesmethylchlorpormazine | 38 |
| Desmethylchlorpromazine | 45 |
| Chlorproethazine | 28 |
| Prochlorperazine | 22 |
| Trifluoperazine | 17 |
| Trifluopromazine | 28 |
| 2-Chloro-10-[2-(dimethylamino)ethyl] phenothiazine | 60 |

TABLE 4-continued

| Compound | Calmodulin IC$_{50}$ (μM) |
|---|---|
| 2-Chloro-10-[2-(dimethyl-amino)butyl] phenothiazine | 40 |
| Promethazine | 340 |
| Quinacrine | 42 |
| Imipramine | 125 |
| 2-Chloroimipramine | 42 |
| Penfluridol | 3 |
| Pimozide | 7 |
| R-6033 | 40 |
| Haloperidol | 65 |

IC$_{50}$ values represent concentration of drug necessary to inhibit by 50% the calmodulin-induced activation of phosphodiesterase.

Example 11

Effect of phenothiazines and structurally related compounds on doxorubicin-sensitive cells The activity of all 31 compounds against cell growth and as modulators of sensitivity to doxorubicin was examined against the doxorubicin-sensitive MCF-7 cell line. Each of the drugs tested were equally potent antiproliferative agents against the doxorubicin-sensitive cell line as compared to their activity against the resistant MCF-7/DOX cell line (data not shown). No compound sensitized the MCF-7 cells to doxorubicin.

Example 12

Drug Accumulation Studies

Whether the difference in the anti-MDR activity of the thioxanthenes could be attributed to differences in their cellular accumulation was determined. After a 3 hour incubation in 3-100 μM concentrations of each drug, cell associated cis and trans-flupenthixol concentrations (nmoles/10$^6$ cells) were 830±80 versus 420±80 at 3 μM, 1420±250 versus 1000±250 at 10 μM and 7000±330 versus 6000±330 at 100 μM.

The effect of the thioxanthenes on the accumulation of doxorubicin in both sensitive and MDR cell lines was also studied. FIG. 5 demonstrates that after a 3 hour incubation in 15 μM doxorubicin, MCF-7/DOX cells accumulated approximately 10-fold less doxorubicin than the sensitive cell line. The addition of 3 uM cis or 6 μM trans-flupenthixol had no significant effect on the accumulation of doxorubicin in the sensitive MCF-7/DOX line. However, they increased by 1.9 and 2.2 fold, respectively, the accumulation of doxorubicin in the resistant MCF-7/DOX cells. Similar results were found after a 3 hour incubation with 1.5 μM and 0.15 μM doxorubicin.

TABLE 5

Effect of Compounds Structurally Related to Phenothiazines on Cell Growth and Multidrug Resistance
IC$_{50}$ values for cell growth and MDR ratios were determined as described in legend to Table 1. Each value represents the mean of quadruplicate determinations.

| Compound | Structure | Cell Growth Inhibition IC$_{50}$ (μM) | MDR Ratio |
|---|---|---|---|
| cis-Flupenthixol | 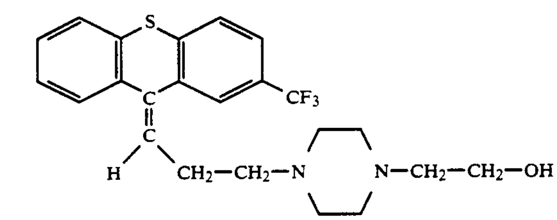 | 24 | 4.8 |
| trans-Flupenthixol | 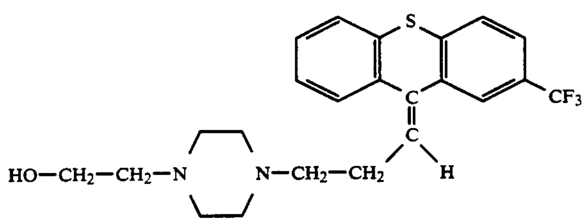 | 25 | 15.2 |
| Quinacrine | 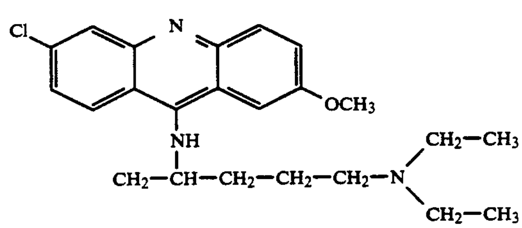 | 3 | 1.3 |
| Imipramine | 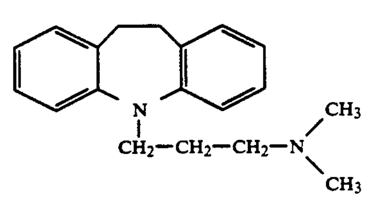 | 19 | 2.5 |

TABLE 5-continued

Effect of Compounds Structurally Related to Phenothiazines on Cell Growth and Multidrug Resistance
$IC_{50}$ values for cell growth and MDR ratios were determined as described in legend to Table 1. Each value represents the mean of quadruplicate determinations.

| Compound | Structure | Cell Growth Inhibition $IC_{50}$ (μM) | MDR Ratio |
| --- | --- | --- | --- |
| 2-Chloroimipramine | 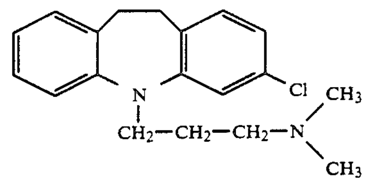 | 20 | 2.0 |
| Penfluridol | 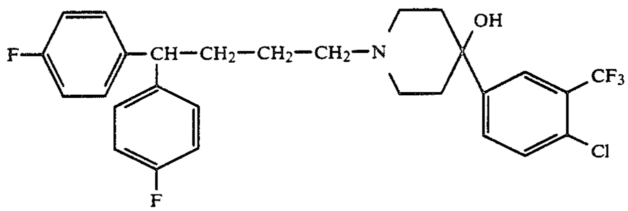 | 3 | 2.0 |
| Pimozide | 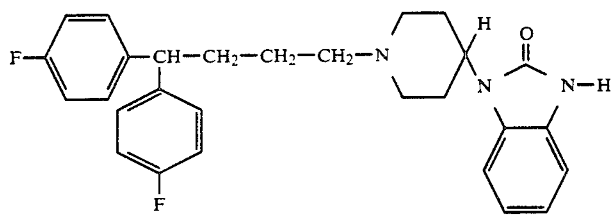 | 50 | 1.3 |
| R-6033 | 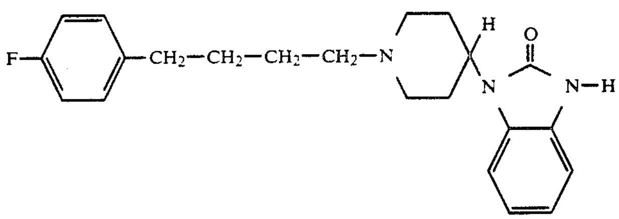 | 27 | 1.1 |
| Haloperidol | 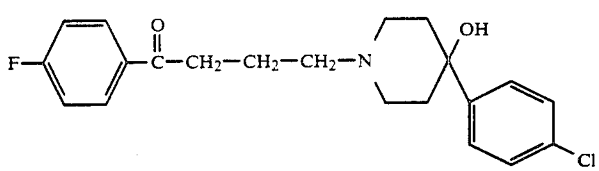 | 750 | 3.3 |

Example 13

Isobologram Analysis

Figure 6:
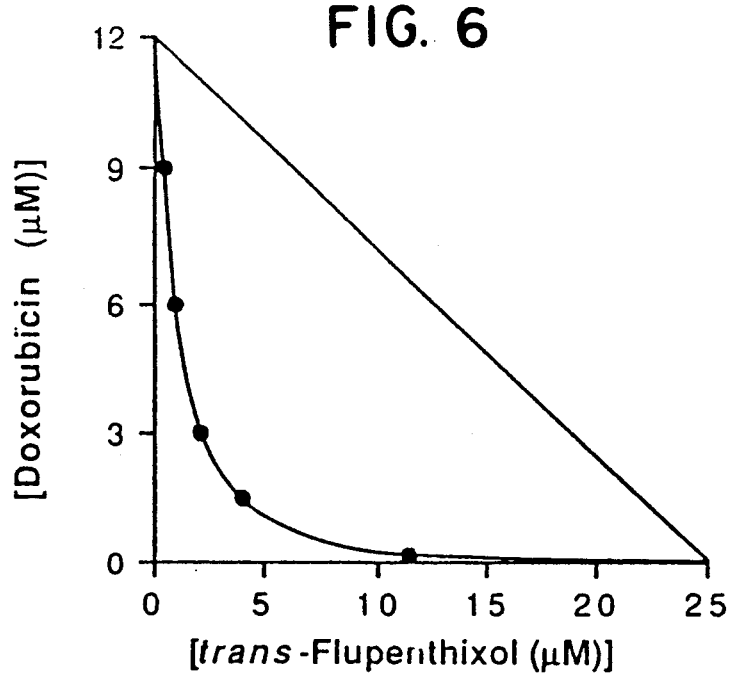
FIG. 6 is a graph depicting an isobologram analysis of the synergistic interaction between doxorubicin and trans-flupenthixol. $IC_{50}$ isobole for inhibition of MCF-7/DOX cell growth by various combinations of doxorubicin and trans-flupenthixol (●) was determined by exposing cells to drug combinations for 48 hours. The straight line represents the predicted $IC_{50}$ isobole for drugs which have additive antiproliferative effects. 12$\mu M$ doxorubicin and 25 $\mu M$ trans-flupenthixol alone caused 50% inhibition of cell growth.

To rigorously study the magnitude of potentiation of doxorubicin by trans-flupenthixol, their multiple drug effects were studied by isobologram analysis. FIG. 6 demonstrates the synergistic action of doxorubicin and trans-flupenthixol, evident by comparing the actual concentrations necessary for 50% inhibition of cell growth to those predicted for drugs which are simply additive.

It will be appreciated that the instant specification and claims are set forth by way of illustration and not limitation, and that various modifications and changes may be made without departing from the spirit and scope of the present invention.

What is claimed is:

1. A clinical method for sensitizing multidrug resistant tumor cells to doxorubicin comprising clinically administering an effective sensitizing amount of trans-flupenthixol and an effective anti-tumor amount of doxorubicin.

2. A method according to claim 1, wherein said cells are human cells.

3. A method according to claim 1, wherein said cells are malignant breast cancer cells.

4. A method according to claim 1, wherein said cells are human leukemia cells.

5. A method according to claim 1, wherein said cells are human colonic carcinoma cells.

6. In an antitumor composition comprising an effective antitumor amount of an antitumor agent, wherein the improvement comprises said antitumor agent being doxorubicin and said composition further comprises an effective sensitizing amount of trans-flupenthixol, wherein said trans-flupenthixol sensitizes multidrug resistant tumor cells to said doxorubicin.

* * * * *

UNITED STATES PATENT AND TRADEMARK OFFICE
CERTIFICATE OF CORRECTION

PATENT NO. : 5,104,858

DATED : April 14, 1992

INVENTOR(S) : HAIT et al

It is certified that error appears in the above-identified patent and that said Letters Patent is hereby corrected as shown below:

Title page, Section [57] Abstract. Replace the Abstract with the following:

-- ABSTRACT OF THE DISCLOSURE

An antitumor composition comprising an anti-tumor effective amount of doxorubicin and an amount of trans-flupenthixol effective to sensitize multi-drug resistant tumor cells to doxorubicin. --

Section [56] References Cited, page 3, right column (line 9 from the bottom):

Change "pastan, I." to --Pastan, I.--.

Signed and Sealed this

Fifth Day of October, 1993

*Attest:*

BRUCE LEHMAN

*Attesting Officer*     Commissioner of Patents and Trademarks